United States Patent
Woodrum

(10) Patent No.: US 6,290,813 B1
(45) Date of Patent: Sep. 18, 2001

(54) SMOOTH TEXTURED WET-LAID ABSORBENT STRUCTURE

(75) Inventor: G. Thomas Woodrum, Chesapeake, VA (US)

(73) Assignee: BASF Corporation, Mount Olive, NJ (US)

(*) Notice: Subject to any disclaimer, the term of this patent is extended or adjusted under 35 U.S.C. 154(b) by 0 days.

(21) Appl. No.: 09/415,349

(22) Filed: Oct. 8, 1999

Related U.S. Application Data

(62) Division of application No. 09/026,002, filed on Feb. 18, 1998, now Pat. No. 5,997,690.

(51) Int. Cl.[7] .................................................. D21H 23/04
(52) U.S. Cl. ..................... 162/158; 162/100; 162/146; 162/168.1; 162/168.3; 162/157.6; 162/177
(58) Field of Search ................... 162/100, 102, 162/146, 157.1, 157.2, 157.6, 164.1, 168.1, 168.3, 175, 177, 183, 109, 111, 113, 158; 604/368–378; 428/372, 375, 393, 357, 361, 378, 359, 221, 294.1, 296.1

(56) References Cited

U.S. PATENT DOCUMENTS

| | | | |
|---|---|---|---|
| 3,669,103 | * 6/1972 | Harper et al. | 604/372 |
| 3,826,711 | * 7/1974 | Schoggen et al. | 162/102 |
| 4,610,678 | * 9/1986 | Weisman et al. | 604/368 |
| 4,986,882 | * 1/1991 | Mackey et al. | 162/109 |
| 5,443,899 | * 8/1995 | Barcus et al. | 428/288 |
| 5,516,585 | * 5/1996 | Young, Sr. et al. | 428/372 |
| 5,531,728 | * 7/1996 | Lash | 604/378 |
| 5,558,661 | * 9/1996 | Roe et al. | 604/385.2 |
| 5,607,550 | * 3/1997 | Akers | 162/102 |
| 5,795,439 | * 8/1998 | Euripides et al. | 162/100 |

* cited by examiner

Primary Examiner—Jose Fortuna
(74) Attorney, Agent, or Firm—David T. Banchik

(57) ABSTRACT

A smooth-textured non-woven, superabsorbent particle-impregnated fibrous structure is disclosed. The web exhibits an improved smooth surface texture. The structure contains from 50% to 80% of ion sensitive SAP having a particle size of less than 200 microns, wood pulp fibers and cellulose acetate fibers, each in preferred specified amounts indicated herein. The superabsorbent, ion sensitive polymer particle-impregnated fibrous structure is made from an aqueous, wet-lay process in which an aqueous furnish comprises solids of fibers and superabsorbent, ion sensitive polymer and dissolved salt, such as preferably, $Na_2SO_4$. The furnish is passed over a moving foraminous support, such as a Fourdrinier wire, and a wet web structure is formed, followed by drying.

5 Claims, No Drawings

SMOOTH TEXTURED WET-LAID ABSORBENT STRUCTURE

This is a divisional of application Ser. No. 09/026,002, filed Feb. 18, 1998 now U.S. Pat. No. 5,997,690.

FIELD OF THE INVENTION

This invention relates to a wet-laid nonwoven structure containing fibers and water insoluble, water-swellable, superabsorbent, ion sensitive polymer particles (SAP) and process for making an absorbent structure. The structure is intended for use in absorbent hygiene products such as diapers, incontinence pads, sanitary napkins and tampons and in wiping materials for mopping up spills of fluids. A wet-laid nonwoven fabric is a fabric comprising fibers which have been deposited from an aqueous suspension onto a moving foraminous support.

BACKGROUND OF THE INVENTION

Fibrous, non-woven, superabsorbent, ion sensitive polymer-impregnated structures are known.

See generally, U.S. Pat. No. 5,167,764, 5,607,550, 5,516,585 and European Publication No. 437,816. Additionally, the following references disclose previously attempted methods of handling superabsorbent or hydrogel ion sensitive polymers to obtain superabsorbent structures. See U.S. Pat. Nos. 3,669,103; 4,610,678; 4,986,882; 5,049,235; 5,137,600; 5,160,789; 5,443,899; 5,531,728; and 5,547,745. See U.S. Pat. No. 5,516,585 teaching the well known binder polymers suggested for use with air laid nonwoven structures containing SAP.

EP-A-437816 discloses a nonwoven wet-laid superabsorbent material produced by the process of blending superabsorbent, ion sensitive polymer particles with a liquid to form a slurry, mixing particles with that slurry, filtering that slurry/fibre mixture to remove a portion of the liquid and drying the superabsorbent slurry/fiber mixture to form a nonwoven wet-laid superabsorbent material.

EP-A-359615 discloses a method for the manufacture of a superabsorbent fibrous structure in which a dry solid absorbent is applied directly to a wet-laid web of cellulosic fibers prior to drying the wet web.

EP-A-273075 discloses a high water-absorbency paper made by sheeting a mixture of wood pulp fiber, water-soluble resin and high water-absorbency resin.

A number of techniques for applying binders to webs of fibers are known. For example, U.S. Pat. No. 4,600,462 of Watt describes a process in which an adhesive binder is sprayed onto one or both surfaces of an air laid cellulose fiber web. Submersion of the web in the adhesive binder is another method disclosed in this patent of applying the binder. Individual binder coated fibers for mixing with other fibers are not produced by this process. A hydrophile solution is also applied to the web. As another example, U.S. Pat. Nos. 4,425,126 and 4,129,132 of Butterworth, et al. describe a fiberous material formed by combining thermoplastic fibers and wood pulp, heat fusing the combined fibers, and thereafter depositing a binder on the heat fused web. Because the fibers are heat fused prior to adding the binder, individual binder coated fibers for mixing with other fibers are not produced by this process.

Absorbent products such as diapers which include particles of a superabsorbent ion sensitive polymer such as crosslinked sodium polyacrylate disposed between layers of wood pulp are known for example from EP-A-257951.

The use of fibers of water-swellable water-insoluble superabsorbent, ion sensitive polymer is disclosed in U.S. Pat. No. 5,607,550, wherein it is taught that incorporation of superabsorbent, ion sensitive polymers in particulate form in the fiber web has significant disadvantages in many respects. The prior art teaches that superabsorbent, ion sensitive polymer particles are less securely retained both during formation of the wet-laid nonwoven structure and when the structure is in further processed during incorporation into an absorbent product. Moreover the art indicates a relatively less uniform dispersion of superabsorbent, ion sensitive polymer particles in the web occurs as opposed to the dispersion of the SAP fiber in the web. It is also taught conventionally that with superabsorbent, ion sensitive polymer particle-impregnated structures, the particles become loosely attached to the fibrous structure of the nonwoven fabric.

In order to provide sufficient absorbency performance necessary for utilization in an absorbent article, it has been found that the loading of superabsorbent in a web must be at least about 50% by weight of the entire structure. However, significant loadings of particles in the fiber structure (such as above about 50% SAP particles on the total weight of the web) require sufficient strength of the wet web in the process Whereas the cost associated with forming fibers of superabsorbent, ion sensitive polymer is inherently higher than that of the particulate SAP, it would be desirable to overcome the aforementioned drawbacks in the use of particles of SAP. Composite structures of fibers impregnated with superabsorbent, ion sensitive polymer particles could greatly reduce the manufacturing cost of end use products such as those aforementioned, however when forming such a structure with 50% or higher loadings of particles of SAP, the web thus formed has a rough texture which can be felt in a disposable article having a top sheet. The texture is telegraphed through the article and may provide undesirable comfort for the user.

Accordingly, there is an unmet need to develop improved superabsorbent, ion sensitive polymer particle-impregnated structures having improved texture for their intended uses. An improved superabsorbent, ion sensitive polymer particle-impregnated structure has been isolated and found to exhibit unexpected smooth texture and surprisingly good absorbency.

SUMMARY OF THE INVENTION

In accordance with the invention there is provided a non-woven, wet-laid, superabsorbent, ion sensitive polymer particle-impregnated fibrous structure having smooth surface texture and which is free of binder polymer. All percentages specified herein are weight percentages. Specifically, the structure comprises from 50% to 80% of ion sensitive SAP having a particle size of less than 250 microns, wood pulp fibers and cellulose acetate fibers, each in preferred specified amounts indicated below. The superabsorbent, ion sensitive polymer particle-impregnated fibrous structure is made from a aqueous, wet-lay process in which an aqueous furnish comprises solids of fibers and superabsorbent, ion sensitive polymer. The aqueous furnish contains 0.2% to 5% or more dissolved salt, which is preferred $Na_2SO_4$. The furnish is passed over a moving foraminous support, such as a Fourdrinier wire, and a wet web structure is formed. The wet web structure is conveyed to an in-line washing zone with a sufficient volume of water, preferably impinging the wet web in a continuous curtain flow, and the washed wet web structure is dried to form the non-woven, wet-laid, superabsorbent, ion sensitive polymer particle-impregnated structure (web).

The wet-laid, superabsorbent, ion sensitive polymer particle-impregnated structure, on a dry weight basis, comprises about 50% to about 80% water insoluble, water swellable ion sensitive polymer (SAP) and about 20% to about 50% fibers (fibrous portion). The fibrous portion of the web comprises 5% to 50% cellulose acetate fibers and 50% to 95% pulp fibers. Preferably the fibrous portion comprises 10% to 50% cellulose acetate fibers and 50% to 90% wood pulp fibers. More preferredly the fiberrous portion comprises 10% to 40% cellulose acetate fibers and 60% to 90% wood pulp fibers. Most preferredly, the fibrous portion comprises 5% to 20% cellulose acetate fibers and 80% to 95% wood pulp fibers.

The wet-laid, superabsorbent, ion sensitive polymer particle-impregnated structure contains from 0% to 35% residual salt in the dried web, preferably from 5% to 35% such residual salt remains, and most preferably 10% to 16% residual salt. The level of residual salt on the total weight of the dried web has been found to correlate inversely with the AUL absorbency performance, described below. The minimum AUL absorbency of the wet-laid, superabsorbent, ion sensitive polymer particle-impregnated web which contains from 5% to 35% residual salt is greater than or equal to about 13 g/g. AUL on the basis of SAP polymer in the sheet is greater than or equal to 19 g/g within the range of 5% to 35% salt. The AUL on the basis of the SAP in the sheet is obtained by dividing the AUL of the web by the percent SAP in the web. Preferably at a lower residual salt content less or equal to about 20%, AUL absorbency per unit SAP in the web is greater than or equal to about 23 g/g. Most preferredly the AUL absorbency per unit of SAP in the web is greater than or equal to 30 g/g and the salt content in the web is between about 10% and 16%.

DETAILED DESCRIPTION OF THE INVENTION

The SAP/fiber web is produced by the process referred to as wet lay processing. An exemplary apparatus known in the art is an inclined wire forming machine, which can be used to form the wet-laid, superabsorbent, ion sensitive polymer particle-impregnated web. The web is transferred from the inclined wire to a horizontal conveyor optionally equipped with vacuum suction ports to further remove processing water. A washing station, typically a trough is mounted at a point along the conveyor to provide a receptacle for wash water applied to the wet web, thereby reducing the level of residual salt in the web. Means for reducing the salt content of the wet web include applying a continuous or discontinuous curtain of water, applying water in a spray pattern, submerging the web in a trough of water, flooding the web and the like, thereby retrieving some salt which has absorbed or adsorbed. After washing, the web is transferred into a means for substantial removal of water. Such means include one or more than one single means, for example, a rotary/thru air dryer, a heated drum dryer, an infrared heating source, hot air blowers, microwave emitting source, and the like, all which are known and used in web drying processes.

All processing waters except that which is driven off in the dryer exhaust, are captured and recycled to the process; these waters are collected in what is identified as the "white water" tank. Web basis weight is controlled by regulating the concentration of superabsorbent ion sensitive polymer and fiber components in the feed or "stock" tank which is fed along with the "white water" at prescribed solids content into the formation chamber (ie inclined wire machine). After exiting the dryer the web is edge trimmed and rolled onto cores. The water contains a salt. The salt can be sodium chloride, or a alkali (NA, K, Li) or alkaline (Ca, Mg, Ba) carbonate, or an alkali or alkaline sulfate. The preferred salt is sodium sulfate because chloride salts contribute to metal stress cracking, and carbonates have the effect of further neutralizing the SAP.

The following test methods were used to determine the properties of the superabsorbent, ion sensitive polymers and the wet-laid, superabsorbent, ion sensitive polymer particle-impregnated structure where indicated.

Residual Sodium Sulfate salt in web is measurable with a Cole Parmer Sulfate Test Kit available from Cole Parmer as Product Code No. 05542-23.

The procedure consists of extracting the sulfate with water and determining the sulfate content from the following procedure.

1. An approx. 2 in. diameter disc of the web sample is cut and weighed. The sample is placed in a beaker containing 150 mls. of deionized water for about three minutes. The supernatent is then poured off and retained for testing as follows:
2. The vial is rinsed with a small portion of the supernatent to be tested. The vial is filled with the supernatent to the lower scoreline (150 ml sample).
3. Phenolpthalein indicator is used to check and adjust to neutral pH, e.g. if the sample turns red, hydrochloric acid 10 N is added with swirling until the color is gone.
4. 1 (one) dipper (contained in the cap) of sulfate indicator powder is added to the vial and allowed to dissolve.
5. Isopropyl alcohol is added to raise the liquid to the upper scoreline followed by swirling.
6. Standard barium chloride solution provided in the kit is added counting dropwise (mixing after each drop) until the yellow color turns to dull red or orange. The number of drops added is recorded.
7. The number of drops of standard barium chloride consumed is multiplied by 25 to indicate the mg per liter (ppm) of sulfate present in the supernatent sample as the following calculation:

8. grams sodium sulfate =

$$\frac{(\text{drops barium sulfate} \times 25 \text{ ppm/drop} \times 150 \text{ ml})}{0.6763}$$

$$\text{percent sodium sulfate} = \frac{\text{grams sodium sulfate} \times 100}{\text{web sample weight}}$$

Absorbency Under Load (AUL) for Particulate SAP

This test is designed to determine the absorbency under load of a particulate superabsorbent, ion sensitive polymer. This is a measure of the amount of saline (0.9% wt/% NaCl aqueous solution) absorbed by the ion sensitive polymer while a predetermined amount of weight is applied to the ion sensitive polymer gel and indicates the effectiveness of the ion sensitive polymer's absorbency in relation to actual use conditions.

Absorbency under load is measured using a plastic petri dish with elevating rods and a 1.241"OD×0.998"ID×1.316" long plexiglass tube with a wire net (100 mesh) at the bottom of the tube. The particle size of the test samples is between 30 to 50 mesh, (through 30 and retained on 50).

A test sample, 0.160±0.01 g is weighed out and recorded as $S_1$. The sample is placed in the plastic tube and is spread evenly over the wire net. A specified weight(e.g. a 100 g, 200 g or 300 g weight yielding 0.3 psi, 0.6 psi and 0.9 psi load, respectively) and a disc are placed on the sample. The assembly (polymer sample, tube, disc and weight) is weighed and recorded as $W_1$. The assembly is then placed in a petri dish containing 40 ml 0.9% saline aqueous solution. After one hour of absorption, the assembly is removed from petri dish and excess saline blotted from the bottom. The assembly is weighed again and this value recorded as $W_2$. Absorbency under load (AUL) is equal to $(W_2-W_1)/S_1$ and is express in g/g.

Absorbency Under Load (AUL/(for web sample)

This test is designed to determine the absorbency under load of a web containing a mixture of superabsorbent polymer and fiberous materials. This is a measure of saline (0.9% wt/% NaCl aqueous) solution absorbed by the web while a predetermined amount of weight is applied to the web and indicates the effectiveness of the web's absorbency in a diaper system under the weight of a baby. Absorbency under load is measured by cutting a 2 in. diameter circular sample with a die cutter. The sample is oven dried for 2 hours and then weighed to +/−0.1 grams. Prior to testing the sample is cooled in a controlled environment (70° C., 50% RH). The sample holder is then dried with a hand-held heating blow-dryer to complete dryness. The sample holder has small feet on the bottom to insure a clearance between the bottom of a saline liquid reservoir and the holder. The volume of saline solution to be added to the liquid reservoir is determined by adding a measured amount of saline solution to the reservoir until the liquid level rises to the top of the perforated plate(s) of the sample holder(s). This volume of saline solution is recorded as X. The volume of the saline to be added to the reservoir is X+120 mls. The circular web sample is placed top side down, inside the holder. The total weight of the sample in it's holder is recorded as the dry weight. A weight (providing load of 0.5 psi) is placed on top of the web sample. The reservoir is filled with X+120 mls. of 0.9% saline solution at a temperature of 23+/−1° C. Simultaneously the sample holder(s) is placed into the solution. After ten minutes of swelling, the sample holder(s) are removed from the reservoir and allowed to drip approximately 60 seconds. The weight is removed. The weight of the wet sample is re-weighed in the sample holder (wet weight). Calculations:

absorbed weight=(total weight of wet sample and holder) minus (total weight of dry sample and holder)

AUL (g/g)=absorbed weight divided by oven dried weight of sample

MATERIALS OF WEB CONSTRUCTION

The fibers used may be filament or staple or a combination of a minor amount of filament and a major amount of staple, or staple fibers of varying lengths. The essential fibers in the web are cellulose acetate (CA) and wood pulp. Optional man-made fibers can be included but are not critical. Polyolefin fibers, polyester fibers and bicomponent fibers could be included. Preferably, all of the fibers used are CA and Pulp staple fibers, generally of length from 1 to 100 mm. In a preferred embodiment, a minor amount (about 20%–30% of the fibrous portion) is polyethylene fiber (type 103 sold under the TREVIRA® trademark), and from about 2 to 10% of the fibrous portion is made of bicomponent fibers sold under the type 105 Celbond® trademark of TREVIRA. The staple fibers are preferably of 10 to 50 mm in length. The greater the length, the greater the strength of the wet web structure up to a point where greater fiber length may adversly affect processing of the furnish, material cost, and web uniformity. Cellulose acetate staple is usually available in lengths of 2 to 50 mm. The more preferred lengths for cellulose acetate are from 0.25 to 0.75 inch (8 to 19 mm), and most preferred are lengths of about 0.5 in. ($\cong$12 mm). Cellulose acetate staple is commercially available from Celanese Acetate, Charlotte, N.C. The denier per filament (dpf) for the cellulose acetate fiber is not critical. Preferably cellulose acetate having 1.8 dpf and 12 mm length (0.5 inch) is used. Longer lengths could be used but at small denier, fiber entanglement can lead to less uniformity in the web.

Wood pulp fluff of typical length of about 8 mm is used in the wet laid nonvoven industry and is also suitable in the practice of the process. Wood pulp fluff fibers can be obtained from well-known chemical processes such as the kraft and sulfite processes. Suitable starting materials for these processes include hardwood and softwood species, such a alder, pine, douglas fir, spruce and hemlock. Wood pulp fibers can also be obtained from mechanical processes, such as ground wood, refiner mechanical, thermomechanical, chemi-mechanical, and chemi-thermomechanical pulp processes. However, to the extent such processes produce fiber bundles as opposed to individually separated fibers or individual fibers, they are less preferred. However, treating fiber bundles is not within the scope of the present disclosure. Recycled or secondary wood pulp fibers and bleached and unbleached wood pulp fibers can also be used. Details of the production of wood pulp fibers are well-known to those skilled in the art. These fibers are commercially available from sources including Weyerhaeuser Company, Buckeye Cellulose, and Rayonier.

Superabsorbent, ion sensitive polymer, as used herein, refers to particulate, water insoluble, but water swellable, materials which will pass through a fine mesh screen (U.S. seive). A fine mesh screen means a screen which allows particles of about 250 micron size or smaller to pass through. For example, particles passing through a 65 mesh screen correspond to particles having a particle size of less than 208 microns. Any metric or equivalent fine mesh screen may be used to give particles having this upper limit of particle size. A sizable portion of the particles used herein pass through a 100 mesh seive and are smaller than 150 microns. A minor portion of the particles will pass through even a 325 mesh seive which corresponds to 45 microns or less.

The superabsorbent-polymers in particulate form as specified above generally fall into three classes, namely, starch graft crosslinked copolymers, crosslinked carboxymethylcellulose derivatives, and hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile/carboxylate copolymer or acrylamide copolymer, a partially neutralized self-crosslinking polyacrylic acid, a partially neutralized, lightly crosslinked polyacrylic acid polymer, carboxylated cellulose, a neutralized crosslinked isobutylene-maleic anhydride copolymer, and the like.

The superabsorbent polymer particles need not be but preferably have a t least a portion of their surface which is crosslinked. Surface crosslinked poly acrylic acid polymers as taught in U.S. Pat. Nos. 4,507,438, 4,541,871, 4,666,983, 5,002,986, 5,140,076, 5,164,459, 5,229,466, 5,322,896, 5,597,873, and EP 509,708 and falling under the following particle size limitations are suitable herein. The particles are typically isolated from the surface treatment of primary SAP particles which have been seived through a selected mesh size screen, e.g., a 65 mesh screen (U.S. seive). The fines represent attrited particle fragments, and it is expected that only a portion of the surface of these particles have surface crosslinking. The prevalent source of fine particle size ion sensitive SAP is from the sifting of the primary hydrogel process stream from the solution polymerization of partially neutralized polyacrylic acid SAP which has been dried, and chopped into granules. The fine particles are recovered from this mass. The fine particles may be recovered from a subsequent process in which primary seived material is treated with crosslinker and seived again. Thus the fine particles used herein may be a mixture of particles which have not been surface crosslinked along with particles which have been sifted from a mass of primary particles which have been treated with surface crosslinker. Commercially available ion sensitive SAP which passes through a 100 mesh screen are sold as SANWET® IM-3500F from Clariant Corp., ARIDALL® from Chemdal, Palatine, Ill. and J550 from Sumitomo Corporation of Japan.

The most preferred, but not essential embodiment of SAP, is recovered from the treatment of primary SAP particles with surface crosslinked from an aqueous crosslinker solution preferably comprising water, a diol selected from a $C_3$ to $C_6$ diol and a crosslinking compound. The water and diol components of the crosslinker solution comprises from about 1.0 to about 6.0 percent by weight based upon the weight of the treated SAP polymer, preferably about 1.5 to about 5.5 percent. The crosslinker solution preferably has a surface tension of less than about 55 dynes per cm. The fine particles are recoverd from this treated mass which has been seived through a screen which retains the primary particles having greater than 65 mesh, U.S. seive.

The web structure is formed as a wet-laid nonwoven by any of the techniques known for wet-laying nonwoven fabrics, for example those described in "Manual of Nonwovens" by R. Krcma (4th Edition 1974, Textile Trade Press, Manchester) at pages 222 to 226. In general, the fiber and particles are wet-laid in a process similar to a conventional papermaking process. The fiber and particles in the aqueous suspension are continuously deposited on the moving foraminous support. The wood pulp fibers may need to be refined, but this is not essential in the practice of the invention. It is preferred to mix the superabsorbent polymer particles into the slurry after refining has been completed.

The furnish can be poured at a controlled rate onto a substantially horizontal mesh screen, or the furnish may be deposited on an inclined mesh screen travelling upwards through the slurry. Alternatively, the furnish can be deposited on a mesh screen which is at the surface of a suction drum. The mesh size of the screen should be such as to allow easy drainage of water but to retain the solids; the most suitable mesh size will generally be in the range 0.2 to 1.5 mm. The mesh can be of metal wire or synthetic polymer, for example polyester filament. The basis weight of the resulting dried web having no more than 0.5% moisture content is preferably from 100 to 500 g/m² (gsm), more preferably from 125 to 275 gsm, and most preferably webs of 150 and 250 gsm are both utilized in a two layered absorbent component for a disposable diaper.

The fiber/SAP/ solids content of the slurry referred to below, whereby salt is not included in reference to slurry solids, are deposited on the foraminous support (wire) is generally in the range 0.1 to 50 g/liter solids content, preferably 0.2 to 20 g/liter, and more preferably 0.2 to ≈5 g/liter. Depending on the feed rate of furnish on the wire and the speed of the line, a solids content in the area of 0.2 to 2 g/liter can be run and conditions adjusted so that a basis weight of from 100 to 500 gsm can be achieved on typical conventional wet-laying machinery. A portion of the water content of the slurry is drained from the deposited fiber/SAP layer while it is supported on the mesh screen, preferably without the aid of suction applied below the screen. Optional compression rolls can be used and may be desired when dryer capacity is limited and particulaly when making higher basis weight webs (350 gsm and above). The solids content of the wet-laid web as it is taken off the mesh screen is preferably at least 5% and most preferably at least 10% by weight, and it is generally not more than 30% and usually not more than 20% by weight prior to treatment with water.

The formed wet web is then passed under the means for reduction of salt, which is preferably a continuous flow of water in the form of a curtain of flowing water. The delivery rate of the water to the web is adjusted to be sufficient to reduce the residual salt content to the desired level in the web.

The extent of salt removal is directly proportional to the wash water flow per sq. area of web. Salt content in the web with no washing step is about 40% when the salt content in the white water is about 4%. Wash water flow rates between 0.5 and 5.0 gal./sq. ft. are preferred. More preferably, in the use of a water curtain, the water flow rate should be between 0.5 and 2 gal./sq ft. Most preferably the water flow rate should be between 0.75 and 1.25 gal./sq. ft. of web.

The wet web, after water treatment is brought to substantial dryness using any suitable techniques generally employed in papermaking including passage of the web around a heated drum, passage between a series of heated rolls, or on a flat bed, through air dryer.

The wet-laid nonwoven structure can optionally include dispersed particles such as silica, a zeolite or a mineral clay, such as kaolin or bentonite. Such particles, which preferably are not used at more than 10% by weight of the nonwoven fabric, can be added to the furnish as described in EP-A-437816 or incorporated in the superabsorbent particles as described in WO-A-92/19799.

EXAMPLES

Comparative Example

Using a small wet-lay web former available under the Bruderhaus® trademark, the following is made:

Superabsorbent, ion sensitive polymer particles having been sifted and retained on a 65 mesh (U.S. seive) screen, and corresponding to particles of greater than 208 microns ) were used in this example. The solids in the slurry comprised about 2.5 g/l solids, with solids comprising 60% of the SAP particles and 40% of the fiber portion. The fiber portion consisted of 100% CA fiber. The $Na_2SO_4$ concentration in the white water was maintained at approximately 4.2%. The furnish was poured on a moving mesh screen at a flow rate of 2 gpm to form a 12 in. wide moving wet web. The web was advanced at the rate of 0.9 m/min. and was passed under a curtain of water flow delivered at a rate of 2.67 gpm. The resulting web was dried over a rotary through air dryer operated at 0.9 meter per min. to yield a structure having a basis weight of 152 gsm. The measured residual $Na_2SO_4$ salt in the web was 34.7%. The AUL for the web was 9.8 g/g, corresponding to AUL per unit SAP of 16.4 g/g.

The dried sheet exhibited a rough texture which can be felt by the skin through a thin nonwoven fabric of the type typically used as a topsheet in absorbent personal hygiene articles. Example 1

Particulate SAP ion sensitive polymer particles which pass through a 65 mesh (U.S. seive) screen, and corresponding to particles of less than 208 microns were used. The solids in the slurry comprised about 2.5 g/l solids, with solids comprising 60% of the SAP and 40% fiber. The fiber portion consisted of approx. 6.25% of 0.5 in. (1.5 dpf) polyester fibers, 40.75% of 0.25 in. (1.8 dpf) cellulose acetate fibers and 40.75% of 8 mm wood pulp fibers and 12.5% polyethylene-sheath/polyester-core, concentric bicomponent fibers (Cellbond) The $Na_2SO_4$ concentration in the white water was maintained at approximately 4.2%. The furnish was poured on a moving mesh screen at a flow rate of 2 gpm to form a 12 in. wide moving wet web. The web was advanced at the rate of 0.9 m/min. and was passed under a curtain of water flow delivered at a rate of 2.67 gpm. The resulting web was dried over a rotary through air dryer operated at 0.9 meter per min. and at 485° F. to yield a structure having a basis weight of 152 gsm. Salt content in the web as determined by the above method was 30.1%. The AUL for the web was 14.2 g/g, corresponding to AUL per unit SAP of 23.7 g/g. The texture of the web was unexpectedly much smoother than the comparative example. The texture of a thin topsheet with the web behind it was more pleasing to the touch. Example 1 exhibited surprisingly better AUL performance versus the comparative example which was essentially of the same basis weight, percent loading of SAP, and similar level of residual salt in the web. The AUL performance of the web of Example 1 was unexpected, since the fine particle size SAP in that web was not expected to perfom as well as the conventional SAP having particle size of 200 microns and higher, and containing more uniform surface crosslinking.

In view of the salt content in the web of Example 1, reduction in the residual salt content of the web to 10% to 25%, will result in an increase in the SAP AUL to greater than 23 g/g.

I claim:

1. A wet-laid, superabsorbent, ion sensitive polymer particle-impregnated structure comprising 50% to about 80% water insoluble, water swellable ion sensitive polymer particles and 20% to 50% fibers, said structure prepared by a process comprising:
   (a) preparing a fiber and water insoluble, water-swellable, superabsorbent, ion sensitive polymer particle containing slurry, essentially all of said particles, before use, have a particle size of less than 250 microns,
   (b) combining said slurry with a water solution containing a salt to form a furnish,
   (c) forming a wet web from said furnish on a moving foraminous support,
   (d) washing said wet web in-line with water, and
   (e) drying said web,
       wherein the residual salt content of the dried web is from less than 40%, and wherein said web has an absorbency under load (AUL) of greater than or equal to 13 g/g.

2. The structure of claim 1 wherein said fibers comprise 10% to 50% cellulose acetate fibers, and 10% to 90% wood pulp fibers, said residual salt content is from 10% to 25%, and wherein said structure has an AUL of greater than or equal to 23 g/g.

3. The structure of claim 2 wherein said cellulose acetate fibers have a length of from 0.25 to 0.5 inches, and said wood pulp fibers have a length of from 0.25 to 0.75 inches.

4. The structure of claim 1 which has a basis weight of from 100 to 500 grams per square meter.

5. The structure of claim 1 comprising 60% to 80% of said water insoluble, water swellable ion sensitive polymer particles and 20% to 40% of said fibers, and wherein said structure has a basis weight of from 125 to 275 grams per square meter.

* * * * *